United States Patent [19]
Miller et al.

[11] Patent Number: 6,130,342
[45] Date of Patent: Oct. 10, 2000

[54] CYP2D FLUORESCENT ASSAY REAGENTS

[75] Inventors: Vaughn P. Miller, Arlington; Charles L. Crespi, Marblehead, both of Mass.

[73] Assignee: Gentest Corporation, Woburn, Mass.

[21] Appl. No.: 09/352,576

[22] Filed: Jul. 12, 1999

Related U.S. Application Data

[60] Provisional application No. 60/092,995, Jul. 16, 1998.

[51] Int. Cl.[7] .......................... C07D 311/12; C07D 311/18
[52] U.S. Cl. ............................. 549/399; 549/400
[58] Field of Search ...................... 549/399, 400

[56] References Cited

U.S. PATENT DOCUMENTS

| | | | |
|---|---|---|---|
| 3,515,721 | 6/1970 | Ritter et al. | 260/247.2 |
| 5,100,914 | 3/1992 | Rendenbach-Mueller et al. | 514/457 |
| 5,247,099 | 9/1993 | Celebuski | 549/289 |
| 5,830,912 | 11/1998 | Gee et al. | 514/457 |
| 5,851,785 | 12/1998 | Aoyama et al. | 435/28 |

FOREIGN PATENT DOCUMENTS

| | | | |
|---|---|---|---|
| 275270 B2 | 2/1992 | Czechoslovakia | C07D 309/38 |
| 1451667 | 7/1966 | France . | |
| 1246754 | 8/1967 | Germany . | |
| 2008109 | 5/1979 | United Kingdom . | |
| 2211500 | 7/1989 | United Kingdom . | |
| WO/92/22545 | 12/1992 | WIPO . | |
| WO/93/15219 | 8/1993 | WIPO . | |

OTHER PUBLICATIONS

Sailaja et al. Synthesis of 7–ethoxy–3–substituted–aminomethyl–4–methylcoumarins. Indian J. Chem., Sect. B, vol. 24B (2), pp. 206–207. (1985). No month found.

*Primary Examiner*—Michael P. Woodward
*Assistant Examiner*—Marjorie A. Moran
*Attorney, Agent, or Firm*—Wolf, Greenfield & Sacks, P.C.

[57] ABSTRACT

Novel fluorescent substrates of the human P450 enzyme CYP2D6 are provided. Also provided are methods for their manufacture and use. These substrates are useful in assessing CYP2D6 enzyme activity and in selecting compounds which inhibit CYP2D6 enzyme activity and, in particular, for identifying potential adverse drug interactions which are mediated by inhibition of CYP2D6 enzyme activity.

17 Claims, 3 Drawing Sheets

CYP2D FLUORESCENT ASSAY REAGENTS

This application claims priority under Title 35 §19(e), of U.S. Provisional Application Ser. No. 60/092,995, filed Jul. 16, 1998, and entitled NOVEL CYP2D FLUORESCENT ASSAY REAGENTS, the entire contents of which are incorporated herein by reference.

FIELD OF INVENTION

This invention relates to the field of drug and xenobiotic metabolism. The invention includes novel cytochrome P450 CYP2D fluorescent probe substrates, methods for their preparation and their use as assay reagents.

BACKGROUND OF THE INVENTION

Cytochromes P450 (CYP) are the principal enzymes for the oxidative metabolism of many drugs, procarcinogens, promutagens, and environmental pollutants. Cytochrome P450 is a heme-containing, membrane-bound, multienzyme system that is present in many tissues in vivo but is present at the highest level in liver. In human liver, it is estimated that there are 15–20 different xenobiotic-metabolizing cytochrome P450 forms. A standard nomenclature based on relatedness of amino acid sequences has been developed. Certain P450 forms (such as CYP2D6 and CYP2C19) are known to be polymorphic in humans and some (such as CYP1A2 and CYP3A4) are regulated in response to environmental chemicals. Competition for metabolism by a particular cytochrome P450 form is a principal mechanism of some clinically significant drug—drug interactions.

Identification of the enzymes responsible for metabolism is becoming an important aspect of drug development. Such identifications consider both the metabolism of the new drug as well as inhibition by the new drug. The identification of enzymes involved in metabolism of the new drug allows prediction, based on knowledge of the ability of coadministered drugs to inhibit the same enzymes, of which coadministered drugs may inhibit the metabolism of the new drug. This information can also be used to predict individual variability based on known metabolic polymorphisms. The identification of the enzymes most sensitive to inhibition by the new drug allows prediction, based on knowledge of which coadministered drugs are metabolized by the same enzyme, of which coadministered drug's metabolism may be inhibited by the new drug. Obtaining information for a series of drug candidates early in the drug discovery process can assist in the choice of the best drug candidate for further development.

CYP2D6 is the only member of the CYP2D subfamily that is expressed in humans. CYP2D6 is responsible for the metabolism of many important drugs, for example: cough suppressants, antiarrhythmics, and psychotropic drugs. CYP2D6 is also polymorphic. About 5–10% of Caucasians and 1–3% of Asians and Africans are deficient in this enzyme. About 5% of Caucasians are ultrarapid metabolizers, have very high levels of CYP2D6 (S. Rendic and F. J. Di Carlo, *Drug Metab. Rev.* 29, 413–580 (1997)). The importance of this P450 in drug metabolism, as well as its variability in activity due to polymorphisms, makes the screening for metabolism and inhibition of this enzyme important in drug development.

Assays for CYP2D have focused on the metabolism of drug molecules or drug candidates. Several drugs are reported to be metabolized by CYP2D6 via O-dealkylation. For example, dextromethorphan is O-demethylated by CYP2D6 (Kupfer, A., Schmid, B., Preisig, R., and G. Pfaff (1984) *Lancet i, p*517.). Substrates such as dextromethorphan or bufuralol are effective in assessing CYP2D activity and inhibition, but are not amenable to high throughput screening assay technology (both require time consuming separation of CYP2D reaction products using HPLC). Also, neither of these substrates has the necessary fluorescent properties that make the substrate useful for in situ fluorescent plate analysis.

We have previously reported the use of the commercially available compound 3-cyano-7-ethoxycoumarin (CEC) as a fluorescent substrate for assessing CYP2D6 activity in a high throughput mode (See Crespi et al. *Anal Biochem.* 248, 188–190, (1997). However, the low enzymatic turnover and poor specificity of this substrate make it of limited utility.

SUMMARY OF THE INVENTION

The present invention relates to novel fluorescent substrates of the human P450 enzyme CYP2D6. These substrates are useful in assessing CYP2D6 enzyme activity and in selecting compounds which inhibit CYP2D6 enzyme activity. Accordingly, the compound and methods of the invention are useful for identifying potential adverse drug interactions which are mediated by inhibition of CYP2D6 enzyme activity.

The compounds of the invention are substrates that are specific for CYP2D and are characterized in having properties which permit the sensitive quantitation of CYP2D activity using in situ fluorescence analysis. To satisfy these requirements, the compounds of the invention include: 1) an ammonium or basic amine functionality for targeting a CYP2D active site, 2) a 7-hydroxycoumarin core for easy fluorescence detection, and 3) an O-alkyl group 5–7 angstroms from the nitrogen which can be easily O-dealkylated by the enzyme.

According to one aspect of the invention, compounds of Formula I are provided:

(a) wherein R1 is an hydrido or a halide;
(b) wherein R2 is an alkyl, a cycloalkyl, or an aryl;
(c) wherein R3 is an hydrido or a halide;
(d) wherein R4 is an hydrido, an alkyl or an aryl;
(e) wherein R5 is an hydrido, an alkyl, or an aryl;
(f) wherein R6 is an alkyl;
(g) wherein R7 is an alkyl;
(h) wherein n is 0, 1, 2,3, or 4;
(i) wherein m is 0 or 1; and
(j) wherein $X^-$ is a negatively charged counter ion.

Each of the substituent R1, R2, R3, R4, R5, R6 and R7 is independently selected from the recited groups above.

Preferably, R1 and R3 are both hydrido or halide. In the most preferred embodiments, one or both of R1 and R3 are hydrido.

Preferably, R2 is an unsaturated alkyl containing from 1 to 5 carbon atoms, inclusive, or an aryl such as benzyl.

Preferably, R4 is an hydrido or an alkyl. The preferred R4 alkyls are saturated alkyls containing from 1–5 carbon atoms, inclusive. The most preferred R4 is an alkyl which is substituted to contain an electron-withdrawing group, e.g., $CF_3$ or CN. These substituted alkyl groups impart different fluorescent properties to the compounds of Formula I.

For compounds of Formula I that are quaternary amines, the preferred R5 alkyls are saturated or unsaturated alkyls containing from 1–5 carbon atoms, inclusive. The most preferred R5 alkyls are methyl or ethyl. The most preferred R5 aryls are benzyl or phenyl.

Preferably, R6 and R7 are, independently, unsaturated alkyls containing from 1–5 carbon atoms, inclusive. More preferably, the R6 and R7 are alkyls containing 1, 2 or 3 carbon atoms and, most preferably, the R6 and R7 alkyls are ethyl.

The compounds of Formula 1 may be tertiary (i.e., m=0) or quaternary (i.e., m=1) amines. Preferably, the compounds of Formula 1 are tertiary amines. For compounds which are quaternary amines, the preferred counter ion is a halide.

In the preferred embodiments, n is 0, 1, 2, 3 or 4 and, more preferably, n is 2.

In the most preferred embodiments, the compound of Formula I is Compound Ia (AMMC, $C_{18}H_{26}NO_3$, Name: 3-[2-(N,N-diethyl-N-methylammonium)ethyl]-4-methyl-7-methoxycoumarin) or Compound Ib ($C_{18}H_{23}F_3NO_3$, Name: 3-[2-(N,N-diethyl-N-methylammonium)ethyl]-7-methoxy-4-trifluoromethylcoumarin) or Compound Ic ($C_{17}H_{20}F_3NO_3$ Name: 3-[2-(diethylamino)ethyl]-7-methoxy-4-trifluoromethylcoumarin) or Compound Id (AMC, $C_{17}H_{23}NO_3$, Name: 3-[2-(diethylamino)ethyl]-7-methoxy-4-methylcoumarin). More preferably, the compound is 3-[2-(N,N-diethyl-N-methylammonium)ethyl]-7-methoxy-4-methylcoumarin).

In the most preferred embodiments, the product produced by the process of allowing a CYP2D enzyme to react with a compound of Formula I is Compound IIa (AMHC, $C_{17}H_{24}NO_3$), Name: 3-[2-(N,N-diethyl-N-methylammonium)ethyl]-7-hydroxy-4-methylcoumarin).

Compound II

Salts of the compounds of Formula I also are embraced within the compounds of the invention. In particular, salts of AMMC and AMC are preferred.

According to yet another aspect of the invention, a composition comprising a compound of Formula I is provided. The compound is present in the composition at a concentration greater than at least 50% by weight. The most preferred compositions contained a concentration of the compound of Formula I that is at least 80%, more preferably at least 90%, and most preferably at least 95% by weight. The preferred compositions are substantially free of detectable reaction product, i.e., the compositions of the invention do not contain levels of the CYP2D-catalyzed conversion product of a compound of Formula II.

The compositions may be contained in vials that are components of a kit for assaying CYP2D enzyme activity. Preferably, the vials contain preselected amounts of the compositions to facilitate dissolution of the contents to achieve a preselected concentration of the compound for performing a CYP2D enzyme assay.

According to yet another aspect of the invention, a method for assaying CYP2D enzyme activity is provided. The method involved contacting a CYP2D enzyme with a compound of Formula I. The assay may be performed in vivo or in vitro. For example, the compounds of the invention (e.g., the compounds of Formula I) can be administered to an animal model for, e.g., locating and, optionally, quantifying. CYP2D enzyme activity (e.g., by observing reaction products in biological fluid or tissue samples of the animal). More preferably, the method for assaying CYP2D enzyme activity is used to detect activity of a CYP2D that may be contained in biological fluid sample or solid sample (e.g., a biopsy sample from liver, brain or intestine) or that may be expressed in a cell-containing or cell-free system (e.g., a microsome containing cDNA-expressed CYP2D). In this manner, conditions associated with deficiencies or over expression of CYP2D enzyme activity can be detected. Thus, the CYP2D enzyme may be contained in a sample that is a liver sample such as a crude homogenate, partially purified, or purified liver enzyme obtained from a biopsy, a cDNA-expressed CYP2D, in hepatocytes, or in microsomes.

According to yet another aspect of the invention, a screening method for identifying agents which inhibit CYP2D enzyme activity is provided. The method involves contacting a CYP2D enzyme with a compound of Formula I in the presence of a putative CYP2D enzyme inhibitor and identifying an agent which inhibits the CYP2D enzyme activity as the CYP2D enzyme inhibitor. In the preferred embodiments, the screening method is a high throughput screening assay.

According to another aspect of the invention, a method for visualizing a CYP2D enzyme is provided. The method involves contacting a CYP2D enzyme-containing sample with a compound of Formula I and subjecting the CYP2D enzyme and the compound to conditions whereby the CYP2D enzyme catalyzes the conversion of the compound of Formula I to a fluorescent product. In the preferred embodiments, the method for visualizing a CYP2D enzyme is performed on a tissue section sample, i.e., the CYP2D enzyme-containing sample is a tissue section such as derived from a biopsy sample.

According to still another aspect of the invention, kits for detecting and/or measuring CYP2D enzyme activity are provided. The kits contain a compound of Formula I and instructions for using the kits to measure CYP2D enzyme activity. The kits may further contain instructions for calculating $K_i$ and/or $IC_{50}$ for a CYP2D inhibitor. The preferred compounds of Formula I are compounds which have a high specificity of binding for the enzyme and for which the enzyme exhibits a high rate of substrate turnover. These parameters typically are reflected in the Km and Vmax values for the enzyme-catalyzed conversion of the substrate (i.e., compound of the invention) to a fluorescent product. In general, a higher relative affinity of the CYP2D enzyme for a first substrate compared to a second substrate is indicated by a lower Km value for the first substrate compared to the second substrate. A higher catalytic turnover for a first substrate compared to a second substrate is indicated by a higher Vmax for the first substrate. The preferred compounds of the invention have a Km of greater than about 50 nM with a Vmax greater than about 0.05 $min^{-1}$. In general, the compounds of the invention have a Km from about 1 to about 100 µM and a Vmax from about 0.05 to about 20 $min^{-1}$, with a preferred range for Km being greater than about 50 nM and a preferred range for Vmax being from about 0.2 to about 20 $min^{-1}$.

According to yet another aspect of the invention, novel fluorescent products are provided. The novel products are compounds of Formula II. In general, the compounds of Formula II are produced as a reaction product of the CYP2D-catalyzed reaction of a substrate that is a compound of Formula I. In general, these compounds have structures that differ from those of the compounds of Formula I in having a hydroxy group at position 7 of the coumarin ring. Formula II is presented below; the substituent groups are as defined above in reference to Formula I:

These and other aspects of the invention as well as various advantages and utilities will be more apparent with reference to the detailed description of the preferred embodiments. All patents, patent publications and references identified in this document are incorporated in their entirety herein by reference.

DETAILED DESCRIPTION OF THE INVENTION

I. Definitions

Throughout this document CYP2D is used in reference to the enzyme which catalyzes the conversion of a compound of the invention to a fluorescent product. It is to be understood that any member of the CYP2D family can be used in any of the enzyme reactions discussed herein and that CYP2D6 represents a particularly preferred embodiment of the invention.

Molecular terms, when used in this application, have their common meaning unless otherwise specified. The term hydrido denotes a single hydrogen atom. The term amino denotes a nitrogen atom containing two substituents that can be the same or different. The amino group substituents are independently selected from the group consisting of hydrido, alkyl, cycloalkyl, and aryl groups.

Alkyl groups can be linear or branched, saturated or unsaturated, and have up to 10 carbon atoms. The preferred alkyl groups are saturated. More preferably, the alkyl groups are "lower alkyl" groups having from 1–5 carbon atoms, inclusive. Exemplary alkyl groups include methyl, ethyl, propyl, butyl, and pentyl. Additional exemplary alkyl groups include isopropyl and tert-butyl.

Aryl groups can contain from 0–4 hetero atoms selected from oxygen, nitrogen and sulfur in a single or fused carbocyclic or heterocyclic ring system, having from 5–15 ring members. One or more hydrogen atoms may also be replaced by a substituent group selected from an acyl, an amino, a carboalkoxy, a carboxy, a carboxyamido, a cyano, a halo, a hydroxy, a nitro, a thio, an alkyl, an aryl, a cycloalkyl, an alkoxy, an aryloxy, a sulfoxy, and a guanido group.

A preferred class of aryl groups are unsubstituted phenyl groups and phenyl groups in which one or more hydrogen have been replaced with an alkyl, alkoxy, aryloxy, or halo group. Exemplary aryl groups include phenyl, phenyl naphthyl, biphenyl, terphenyl, pyridinyl, and various other phenyl derivatives.

Cycloalkyl groups have, preferably, saturated or partially unsaturated ring systems, each containing zero to four hetero atoms selected from oxygen, nitrogen and sulfur in a single or fused carbocyclic or heterocyclic ring system having from three to fifteen ring members. One or more hydrogen atoms may also be replaced by a substituent group selected from acyl, amino, carboalkoxy, carboxy, carboxyamido, cyano, halo, hydroxy, nitro, oxo, thio, alkyl, aryl, cycloalkyl, alkoxy, aryloxy, and guanido groups or two substituents together may form a fused cycloalkyl ring. Examples of a cycloalkyl group include cyclopropyl, cyclobutyl, cyclohexyl, cycloheptyl, morpholinyl, piperidinyl, and pyrolidinyl. An alkoxy group denotes an oxygen atom substituted with an acyl, alkyl or cycloalkyl group. Examples include methoxy, tert-butoxy, benzyloxy, and cyclohexyloxy. An aryloxy groups denotes an oxygen atom substituted with an aryl group. Examples of aryloxy groups are phenoxy, 4-carbobenzyloxyphenoxy, 4-phenoxyphenoxy. Preferred aryloxy groups are phenoxy and substituted phenoxy groups. Sulfoxy groups comprise a hexavalent sulfur atom bound to two or three substituents selected from the group consisting of oxo, alkyl, aryl and cycloalkyl groups, wherein at least one of said substituents is oxo.

The acceptable salts of the compounds of Formula I include acid addition salts. Such salts that are intended for administration to an animal, e.g., an animal model for metabolic studies, can be a pharmaceutically acceptable salt, i.e., the salt is one which is non-toxic and acceptable for administration to an animal in accordance with government regulations. The term salts embraces salts commonly used to form addition salts of ammonium ions. The nature of the salt is not critical. Suitable acid addition salts of the compounds of Formula I may be prepared from an inorganic acid or an organic acid. Examples of such inorganic acids are hydrochloric, hydrobromic, hydroiodic, nitric, carbonic, sulfuric and phosphoroic acid. Appropriate organic acids may be selected from aliphatic, cycloaliphatic, aromatic, arylaliphatic, heterocyclic, carboxylic, and sulfonic classes of organic acids, examples of which are formic, acetic, propionic, succinic, glycolic, gluconic, maleic, embonic (pamioc), methanesulfonic, ethanesulfonic, 2-hydroxyethanesulfonic, panththenic, benzenesulfonic, toluenesulfonic, sulfanilic, mesylic, cyclohexylaminosulfonic, stearic, algenic, b-hydroxybutyric, malonic, galactic, and galacturonic acid. All of these salts may be prepared by conventional means from the corresponding compound of Formula I by treating, for example, the compound of Formula I with the appropriate acid.

II. Description

The invention provides compounds of Formula I, methods for their manufacture and use. The compounds of Formula I are useful for assaying the activity of CYP2D. The compounds are particularly useful for measuring the potential inhibition of CYP2D6, preferably in a high throughput screening assay. For example, the invention provides a method for assaying CYP2D which involves contacting a CYP2D enzyme with a compound of Formula I under the conditions in which the CYP2D enzyme interacts with the compound of Formula I and catalyzes dealkylation at the 7 position of the compound to form a 7-hydroxy coumarin product. Such conditions are known to those skilled in the art (see also, e.g., the Examples for conditions). This method can be performed using in vivo or in vitro sources of enzyme CYP2D. In a further aspect, the invention provides a method for assessing the potential CYP2D inhibition of a test chemical, preferably in a high throughput screening assay. Such conditions are known to those skilled in the art and are exemplified in the Examples.

The present invention comprises, in a first aspect, compounds of Formula I:

(GENERIC STRUCTURE FOR A SUBSTRATE)

(a) wherein R1 is an hydrido or a halide (e.g., F, Cl, Br, and I);

(b) wherein R2 is an alkyl (e.g., methyl, ethyl, propyl, butyl, and pentyl), a cycloalkyl (e.g., cyclohexyl) or an aryl (e.g., benzyl);

(c) wherein R3 is an hydrido or a halide (e.g., F, Cl, Br, and I);

(d) wherein R4 is an hydrido, an alkyl (e.g., methyl, ethyl, $CF_3$, CN), or an aryl (e.g., benzyl);

(e) wherein R5 is an hydrido, an alkyl (e.g., methyl, ethyl), or an aryl (e.g., benzyl);

(f) wherein R6 is an alkyl (e.g., methyl, ethyl, propyl);

(g) wherein R7 is an alkyl (e.g., methyl, ethyl, propyl);

(h) wherein n is 0, 1, 2,3, or 4;

(i) wherein m is 0 or 1 and (j) wherein $X^-$ is a negatively charged counter ion (e.g., a halide such as Cl, F, Br, I, or an organic base such as AcO—).

Each of the substituent R1, R2, R3, R4, R5, R6 and R7 is independently selected from the recited groups above.

Preferably, R1 and R3 are both hydrido or halide. For example, each of R1 and R3 can be fluorine, chlorine, bromine, or iodine. The preferred halide is fluorine. More preferably, one or both of R1 and R3 are hydrido.

Preferably, R2 is an alkyl, a cycloalkyl or an aryl. More preferably, R2 is an alkyl or an aryl. The preferred R2 alkyls are unsaturated alkyls containing from 1 to 5 carbon atoms, inclusive. The preferred R2 aryl is benzyl.

Preferably, R4 is an hydrido or an alkyl. The R4 alkyl can be substituted or unsubstituted; however, the preferred R4 alkyls are saturated alkyl containing from 1–5 carbon atoms, inclusive. The most preferred R4 is an alkyl which is substituted to contain an electron-withdrawing group, e.g., $CF_3$ or CN. These substituted alkyl groups impart different fluorescent properties to the compounds of Formula I. Thus, by altering the identity of the R4 group, one can predictably change the excitation and emission wavelengths of the fluorescent product which results from the action of CYP2D on a compound of Formula I.

For compounds of Formula I that are quaternary amines, R5 is selected from the group consisting of an hydrido, an alkyl or an aryl. The preferred R5 alkyls are saturated or unsaturated alkyls containing from 1–5 carbon atoms, inclusive. The most preferred R5 alkyls are methyl or ethyl. The most preferred R5 aryl is benzyl.

The R6 and R7 groups are independently selected from the group consisting of an hydrido, an alkyl and an aryl. The more preferred R6 and R7 groups are unsaturated alkyls containing from 1–5 carbon atoms, inclusive. The more preferred R6 and R7 are alkyl groups containing 1, 2 or 3 carbon atoms and, most preferably, the R6 and R7 alkyls are ethyl.

In certain embodiments, the compounds of Formula I are selected from the group consisting of compounds in which: $R^1$ and $R^3$ are fluoro; $R^2$ is methyl, ethyl, or benzyl; and $R^4$ is trifluoromethyl or cyano.

The compounds of Formula I may be tertiary (i.e., m=0) or quaternary (i.e., m=1) amines. Quaternary amines of Formula I require a negatively charged counter ion, such as a halide or an organic base. The halide can be a fluorine, a chlorine, a bromine, or an iodine, with chlorine being preferred. The organic bases that can be counter ions include formate, acetate, maleate, and succinate.

In the preferred embodiments, n is 0, 1, 2, 3 or 4 and, more preferably, n is 2.

In the most preferred embodiments, the compound of Formula I is Compound Ia (AMMC, $C_{18}H_{26}NO_3$, Name: 3-[2-(N,N-diethyl-N-methylammonium)ethyl]-7-methoxy-4-methylcoumarin) or Compound Ib ($C_{19}H_{23}F_3NO_3$ Name: 3-[2-(N,N-diethyl-N-methylammonium)ethyl]-7-methoxy-4-trifluoromethylcoumarin) or Compound Ic ($C_{17}H_{20}F_3NO_3$ Name: 3-[2-(diethylamino)ethyl]-7-methoxy-4-trifluoromethylcoumarin) or Compound Id (AMC, $C_{17}H_{23}NO_3$, Name: 3-[2-(diethylamino)ethyl]-7-methoxy-4-methylcoumarin). More preferably, the compound is 3-[2-(N,N-diethyl-N-methylammonium)ethyl]-7-methoxy-4-methylcoumarin).

In the most preferred embodiments, the product produced by the process of allowing a CYP2D enzyme to react with a compound of Formula I is a compound of Formula II. Exemplary compounds of Formula II include Compound Ia (AMHC, $C_{17}H_{24}NO_3$), Name: 3-[2-(N,N-diethyl-N-methylammonium)ethyl]-7-hydroxy-4-methylcoumarin):

COMPOUND IIa

More particularly, Compound II is the reaction product of the reaction of CYP2D using the substrate, AMMC (Compound Ia).

Salts of the compounds of Formula I also are embraced within the compounds of the invention.

According to yet another aspect of the invention, a composition comprising a compound of Formula I is provided. The compound is present in the composition at a concentration greater than at least 50% by weight, and, more preferably is present in the composition at a concentration greater than at least 75% by weight. The most preferred compositions contained a concentration of the compound of Formula I that is at least 80%, more preferably at least 90%, and most preferably at least 95% by weight.

The compositions may be contained in vials that are components of a kit for assaying CYP2D enzyme activity. The vials may contain preselected amounts of the compositions to facilitate dissolution of the contents to achieve a preselected concentration of the compound for performing a CYP2D enzyme assay. Accordingly, in certain embodiments of the invention, the compositions contain the appropriate buffers for performing an enzyme reaction in which the compound of Formula I serves as the substrate to form a fluorescent product.

According to yet another aspect of the invention, a method for assaying CYP2D enzyme activity is provided. The method involved contacting a CYP2D enzyme with a compound of Formula I. The method for assaying CYP2D enzyme activity is used to detect activity of a CYP2D that may be contained in biological fluid sample or solid sample (e.g., a biopsy sample from liver, brain or intestine) or that may be expressed in a cell-containing or cell-free system (e.g., a microsome containing cDNA-expressed CYP2D). In this manner, conditions associated with deficiencies or over expression of CYP2D enzyme activity can be detected.

According to yet another aspect of the invention, a screening method for identifying agents which inhibit CYP2D enzyme activity is provided. The method involves contacting a CYP2D enzyme with a compound of Formula I in the presence of a putative CYP2D enzyme inhibitor and identifying an agent which inhibits the CYP2D enzyme activity as the CYP2D enzyme inhibitor. In the preferred embodiments, the screening method is a high throughput screening assay. More preferably, the screening assay is performed in a multiwell (e.g., microtiter) plate or a container for containing a relatively small volume, e.g., the compound of Formula I is contacted with the putative CYP2D enzyme inhibitor and the CYP2D enzyme in a microtiter plate well or a small vial. In certain embodiments, the compounds of Formula I can be provided in the microtiter plate well or small vial. For example, the compounds of Formula I can be distributed into one or more vials, which are then lyophilized or otherwise dried to provide a product having an enhanced shelf life. If the product is provided for use in a kit for measuring CYP2D enzyme activity, the kit can further contain instructions for redissolving the compound of Formula I and, optionally, an appropriate buffer (e.g., enzyme reaction buffer) for effecting the dissolution.

According to another aspect of the invention, a method for visualizing a CYP2D enzyme is provided. The method involves contacting a CYP2D enzyme-containing sample with a compound of Formula I and subjecting the CYP2D enzyme and the compound to conditions whereby the CYP2D enzyme catalyzes the conversion of the compound of Formula I to a fluorescent product. In the preferred embodiments, the method for visualizing a CYP2D enzyme is performed on a tissue section sample, i.e., the CYP2D enzyme-containing sample is a tissue section such as derived from a biopsy sample.

According to still another aspect of the invention, kits for detecting and/or measuring CYP2D enzyme activity are provided. The kits contain a compound of Formula I and instructions for using the kits to measure CYP2D enzyme activity. The preferred compounds of Formula I are compounds which have a high specificity of binding for the enzyme and for which the enzyme exhibits a high rate of substrate turnover. These parameters typically are reflected in the Km and Vmax values for the enzyme-catalyzed conversion of the substrate (i.e., compound of the invention) to a fluorescent product. In general, a higher relative affinity of the CYP2D enzyme for a first substrate compared to a second substrate is indicated by a lower Km value for the first substrate compared to the second substrate. A higher catalytic turnover for a first substrate compared to a second substrate is indicated by a higher Vmax for the first substrate. The preferred compounds of the invention have a Km of greater than about 50 nM with a Vmax greater than about 0.05 min$^{-1}$. In general, the compounds of the invention have a Km from about 1 to about 100 $\mu$M and a Vmax from about 0.05 to about 20 min$^{-1}$, with a preferred range for Km being greater than about 50 nM and a preferred range for Vmax being from about 0.2 to about 20 min$^{-1}$.

According to yet another aspect of the invention, novel fluorescent products are provided. The fluorescent products are produced as a reaction product of the CYP2D-catalyzed reaction of a substrate that is a compound of Formula I. In general, these compounds (the compounds of Formula II) have structures that differ from those of the compounds of Formula I in having a hydroxy group at position 7 of the coumarin ring.

General Synthetic Procedures

General Procedure I

A compound of Formula II or a commercially available reagent is converted to a compound of Formula I that is a quaternary amine by treatment with reagent A and a base such as potassium carbonate in an appropriate solvent such as tetrahydrofuran, acetone, dimethyl sulfoxide, acetonitrile, or dimethylformamide at temperatures ranging from 0° C. to 75° C. A preferred compound for performing this reaction is Compound IIa (Registry No. 15776-59-7, Name: 3-[2-(diethylamino)ethyl]-7-hydroxy-4-methylcoumarin hydrochloride), available commercially (Aldrich Chem. Co., Milwaukee, Wis.), to yield a preferred compound of Formula I, Compound Ia (AMMC).

wherein each of R1, R2, R3, R4, R5, R6, R7, m, and n are defined as above; wherein A is an alcohol alkylating reagent such as iodomethane, iodoethane, benzylbromide, diazomethane or (trimethylsilyl)diazomethane.

General Procedure 2

Compound 1, or a commercially available reagent, is converted to compound 3 by reaction with a dialkyl malonate, compound 2, in an appropriate solvent such as tetrahydrofuran, diethylether, or dimethylformamide at temperatures ranging from 0° C. to 100° C. In the reactions which follow, each of the intermediates is optionally purified via the purification methods described in the specific examples.

Reaction 2 wherein each of R2, R6, R7 and n are defined as above; wherein Lg is a leaving group such as a halide or tosylate; wherein M is a monovalent metal such as sodium, lithium, or potassium.

Compound 3 is converted to compound 4 by deesterification with B, decarboxylation with C and esterification with D in an appropriate solvent such as water at temperatures ranging from 0° C. to 100° C.

Reaction 3 wherein each of R2, R6, R7 and n are defined as above; wherein B is a base such as sodium hydroxide or lithium hydroxide; wherein C is an acid such as hydrochloric acid; wherein D is an alcohol such as methanol, or ethanol.

Compound 4 is converted to Compound 6 via the procedure described in Linderman and Graves *J. Org. Chem.*, 54, 661–668, (1989). Compound 4 is converted to its respective enolate with E in an appropriate solvent such as tetrahydrofuran at −78° C. and then acylated by the addition of compound 5 to form compound 6 at temperatures ranging from 0–75° C.

Reaction 4 wherein each of R2, R4, R5, R6, R7 and n are as defined above; wherein E is a base such as lithium diisopropylamine (LDA).

Compound 6 is converted to a compound of Formula I by treatment with Compound 7 and an acid such as trifluoroacetic acid via the procedure described in Bayer et. al., *J. Fluorine Chem.*, 20, 187–202, (1982) at temperatures ranging from 0–200° C.

Reaction 5 wherein each of R1, R2, R3, R4, R6, R7 and n are defined as above.

General Procedure 3

Compound 8, a commercially available compound or synthesized using General Procedure 2, is converted to compound 10 by treatment with Compound 9 either without a solvent or with an appropriate solvent such as acetone, tetrahydrofuran, or dimethylformamide at temperatures ranging from 0–100° C.

Reaction 6

-continued (10)

wherein each of R1, R2, R3, R4, R5, R6, R7, X⁻, and n are defined as above; wherein R8 is hydrido, an alkyl, a cycloalkyl, or an aryl; wherein X is a halide. If R8 is hydrido, then compound 10 is of Formula II. If R8 is, an alkyl, a cycloalkyl, or an aryl; then Compound 10 is of Formula I.

General Procedure 5

Compound 6, a commercially available compound or synthesized using General Procedure 2, is converted to Compounds of Formula II by treatment with Compound 11 and an acid such as trifluoroacetic acid via the procedure described in Bayer et. al., *J. Fluorine Chem.*, 20, 187–202, (1982) at temperatures ranging from 0–200° C.

wherein each of R1, R2, R3, R4, R6, R7 and n are defined as above.

EXAMPLES

The following examples are detailed descriptions of the methods of making the compounds of Formula I and Formula II. These detailed preparations fall within the scope of, and serve to exemplify, the above described General Procedures which form part of the invention. These Examples are presented for illustrative purposes only and are not intended to limit the scope of the invention. Table I is a list of specific examples within Formulas I and II.

Example 1

Preparation of 3-[2-(N,N-diethyl-N-methylammonium) ethyl]-7-methoxy-4-methylcoumarin (Compound Ia)

To a solution of 3-[2-(diethylamino)ethyl]-7-hydroxy-4-methylcoumarin hydrochloride (0.5 g) in acetone (200 ml) was added potassium carbonate (5 g) and iodomethane (2.25 g). After stirring at room temperature for 24 hours, the mixture was dried over anhydrous sodium sulfate, filtered, and evaporated to dryness to give 3-[2-(N,N-diethyl-N-methylammonium)ethyl]-7-methoxy-4-methylcoumarin (Ia) as a white powder. $^1$H-NMR (CD$_3$OD) δ 7.75 (d, 1H, ArH), 7.10–6.91 (m, 1H, ArH), 6.92–6.90 (m, 1H, ArH), 3.89 (s, 3H, OCH$_3$), 3.52–3.42 (m, 2H, NCH$_2$), 3.34–3.30 (m, 2H, ArCH$_2$), 3.12–3.05 (m, 5H, NCH$_2$, NCH$_3$), 2.52 (s, 3H, ArCH$_3$), 1.46–1.41 (m, 6H, CH$_2$CH$_3$) m.p. 245–246.5 C. Anal. Calcd. for C$_{18}$H$_{26}$INO$_3$: C, 49.71; H, 6.12; I, 29.18; N, 3.22. Found: C, 49.37; H, 6.11; I, 29.21; N, 3.24.

Example 2

Preparation of 3-[2-(diethylamino)ethyl]-7-methoxy-4-trifluoromethylcoumarin (Compound Ic)

To a stirred solution of diethyl malonate (1, 110.8 g, 0.691 mole) in tetrahydrofuran (400 mL) was added sodium (15.9 g, 0.691 mole) and the resulting solution was boiled overnight. 2-Diethylaminoethyl chloride in ethyl ether (100 mL) was then added to this solution at 50–60° C., after the addition was complete the temperature was increased and the solution boiled for 5 h. The reaction mixture was then cooled under a nitrogen atmosphere, poured onto ice and extracted with diethyl ether and then dried over anhydrous sodium sulfate. Evaporation of the solvent under reduced pressure gave the crude residue which was chromatographed on silica gel (50% ethyl ether in hexanes with 2% methanol and 2% ammonium hydroxide) and afforded ethyl (2-carboxyethyl-4-diethylamino)butyrate (yellow oil, 128.2 g, 75%).

Ethyl (2-carboxyethyl-4-diethylamino)butyrate (128.2 g, 0.495 mole), in tetrahydrofuran (600 mL) and methanol (200 ml.) was hydrolyzed with lithium hydroxide (45.7 g, 1.09 mole) in water (200 mL) by stirring at room temperature under a nitrogen atmosphere overnight. The solvents were removed and the residue acidified with 290 mL of 6M hydrochloric acid (to pH=1–2) and boiled overnight. The reaction mixture was cooled. Methanol (3 L) and concentrated hydrochloric acid (30 mL) were then added and the resulting solution boiled overnight. The methanol was removed and the residue cooled and neutralized to pH~9 with concentrated ammonium hydroxide. The product was extracted with methylenechloride and dried over anhydrous sodium sulfate. Concentration under reduced pressure gave methyl (4-diethylamino)butyrate (yellow oil, 45.7 g, 53%).

A 5 L 4-neck flask was fitted with a mechanical stirrer and two addition funnels. To this flask was added diisopropyl amine (43.87 g, 0.433 mole) in tetrahydrofuran (500 mL) under a nitrogen atmosphere. The solution was then cooled to −78° C. and to this was then added 2.5M n-butyllithium in hexanes (173.5 mL, 0.433 mole). The resulting solution was then stirred at −78° C. for 30 min. Methyl-4-diethylaminobutyrate, in tetrahydrofuran (300 mL) was then added and the resulting solution stirred at −78° C. for 2 h. Then trifluoroethyl acetate (82.13 g, 0.578 mole) in tetrahydrofuran (200 mL) was added. The reaction mixture was then stirred at room temperature overnight. The reaction was cooled to 0° C. and quenched with water (50 mL). The solution was then stirred for 30 min. and then concentrated in vacuo. The residue was diluted with methylenechloride, washed with water, brine, and dried over anhydrous sodium sulfate. Evaporation of the solvents under reduced pressure gave methyl (2-trifluoroaceto-4-diethylamino)butyrate as a brown semisolid (60.4 g, 78%).

To a cooled (0° C.) stirred solution of methyl (2-trifluoroaceto-4-diethylamino)butyrate, (32.33 g, 0.12 mole) and methyl resorcinol (14.92 g, 0.12 mole) was added trifluoroacetic acid (60 mL) and the resulting solution boiled for 3 days. The reaction mixture was cooled, neutralized with ammonium hydroxide (pH 9.5–10), and extracted with ethyl acetate. The organic phase was then washed with water, brine, and then dried over anhydrous sodium sulfate. Evaporation of the solvent under reduced pressure gave the crude solid which was chromatographed on silica gel (40% ethyl acetate/hexane →80% ethyl acetate /hexane) and gave 3-[2-(diethylamino)ethyl]-7-methoxy-4-trifluoromethylcoumarin (Compound Ic) as a white solid 3.3 g [Rf~0.3 (70% ethyl acetate/hexane), 7.9%] $^1$H-NMR (CDCl$_3$) δ 7.70–7.64 (m, 1H, ArH), 6.90–6.83 (m, 2H ArH), 3.88 (s, 3H, OCH$_3$), 3.05–2.96 (m, 2H, ArCH$_2$), 2.73–2.55 (m, 6H, NCH$_2$), 1.10–1.04 (m, 6H, NCH$_2$CH$_3$). m.p. 75–76.5 C. Anal. Calcd. for C$_{17}$H$_{20}$F$_3$NO$_3$: C, 59.77; H, 6.0; N, 4.03. Found: C, 60.20; H, 5.96; N, 3.74.

Example 3
Preparation of 3-[2-(N,N-diethyl-N-methylammonium) ethyl]-7-methoxy-4-trifluoromethylcoumarin iodide (Compound Ib)

3-[2-(diethylamino)ethyl]-7-methoxy-4-trifluoromethylcoumarin (Compound Ic) (100 mg, 0.29 mmole) in methyliodide (1 mL) was stirred in a closed reaction vial for 4 h. The white solid was then filtered, washed with ethyl acetate, and pentane, and gave 120 mg, (85%) of 3-[2-(N,N-diethyl-N-methylammonium)ethyl]-7-methoxy-4-trifluoromethylcoumarin iodide (Compound Ib). $^1$H-NMR (DMSO-d$_6$) δ 7.70–7.67 (m, 1H, ArH), 7.18–7.17 (m, 1H, ArH), 7.10–7.00 (m, 1H, ArH), 3.92 (s, 3H, OCH$_3$), 3.45–3.39 (m, 4H, NCH$_2$), 3.34–3.27 (m, 2H, NCH$_2$), 3.18–3.09 (m, 2H, ArCH$_2$), 3.03 (s, 3H, NCH$_3$), 1.28–1.25 (m, 6H, NCH$_2$CH$_3$). M.p. 214 C. Anal. Calcd. for C$_{18}$H$_{23}$F$_3$INO$_3$ C, 44.55; H, 4.78; N, 2.89. Found: C, 44.49; H, 4.79; N, 2.80.

Example 4
Preparation of 3-[2-(diethylamino)ethyl]-7-hydroxy-4-trifluoromethylcoumarin (Compound IIc)

To a cooled (0° C.) stirred solution of methyl (2-trifluoroaceto-4-diethylamino)butyrate 7 (10.9 g, 0.04 mole) and resorcinol (4.46 g, 0.04 mole) was added trifluoroacetic acid (33.5 ml,) and the resulting solution boiled for 3 days. The reaction mixture was cooled, neutralized with ammonium hydroxide (pH 8–9), and extracted with ethyl acetate. The organic phase was then washed with water, brine, and dried over anhydrous sodium sulfate. Evaporation of the solvent under reduced pressure gave the crude residue which was chromatographed on silica gel (40–70% ethyl acetate/hexane) which afforded the product 3-[2-(diethylamino)ethyl]-7-hydroxy-4-trifluoromethylcoumarin (Compound IIc) as a yellow solid (1.15 g, 8.6%). Rf~0.3 (70% EtOAc/hexane), $^1$H-NMR (acetone-d$_6$) δ 7.65–7.62 (m, 1H, ArH), 6.94–6.90 (m, 1H, ArH), 6.81–6.80 (m, 1H, ArH), 2.96–2.93 (m, 2H, ArCH$_2$), 2.69–2.61 (m, 2H, NCH$_2$), 2.58–2.51 (m, 4H, NCH$_2$), 1.02–0.97 (m, 6H, NCH$_2$CH$_3$). m.p. 122–123 C. Anal. Calcd. for C$_{16}$H$_{18}$F$_3$NO$_3$: C, 58.36; H, 5.51; N, 4.25. Found: C, 58.49; H, 5.62; N, 4.13.

Example 5
Preparation of 3-(2-(N,N-Diethyl-N-methylammonium) ethyl)-7-hydroxy-4-trifluoromethylcoumarin iodide (Compound IIb)

To a stirred solution of 3-[2-(diethylamino)ethyl]-7-hydroxy-4-trifluoromethylcoumarin (Compound IIc) (60 mg, 0.18 mmole) in acetone (0.3 mL) was added methyliodide (0.5 mL) then the resulting solution stirred for 5 mins. The white solid that formed was filtered and washed with acetone and pentane. In this manner the product 3-(2-(N,N-Diethyl-N-methylammonium)ethyl)-7-hydroxy-4-trifluoromethylcoumarin iodide (Compound IIb) was isolated as a white solid (47 mg, 53.5%). $^1$H-NMR (DMSO-d$_6$) δ 7.64–7.60 (m, 1H, ArH), 6.99–6.90 (m, 1H, ArH), 6.84–6.83 (m, 1H, ArH), 3.45–3.39 (m, 4H, NCH$_2$), 3.34–3.25 (m, 2H, NCH$_2$), 3.14–3.05 (m, 2H, ArCH$_2$), 3.02 (s, 3H, NCH$_3$), 1.30–1.25 (m, 6H, NCH$_2$CH$_3$). M.p. 220–221 C. Anal. Calcd. for C$_{17}$H$_{21}$F$_3$INO$_3$, 0.6 H$_2$O: C, 42.36; H, 4.64; N, 2.91; I, 26.32. Found: C, 41.98; H, 4.84; N, 2.85; I, 26.30.

TABLE I

| # | Structure | General Procedure |
|---|---|---|
| Ia | (7-methoxy-4-methyl-coumarin with 3-[2-(N,N,N-triethylammonium)ethyl], I⁻) | 1 |
| Ib | (7-methoxy-4-CF$_3$-coumarin with 3-[2-(N,N,N-triethylammonium)ethyl], I⁻) | 3 |
| Ic | (7-methoxy-4-CF$_3$-coumarin with 3-[2-(diethylamino)ethyl]) | 2 |
| IIb | (7-hydroxy-4-CF$_3$-coumarin with 3-[2-(N,N,N-triethylammonium)ethyl], I⁻) | 3 |
| IIc | (7-hydroxy-4-CF$_3$-coumarin with 3-[2-(diethylamino)ethyl]) | 4 |

Biological Evaluation.

The evaluation of compounds of Formula I for usefulness as CYP2D substrates includes: (1) Enzyme kinetics for the compounds of Formula I were performed using cDNA-expressed CYP2D; (2) The specificity of the compounds of Formula I as substrates for CYP2D were examined using a panel of cDNA-expressed human P450 enzymes; (3) The specificity of the compounds of Formula I as substrates for CYP2D were examined in human liver microsomes; and (4) The IC$_{50}$ values for known inhibitors of CYP2D6, measured in a high throughput screening assay, of compounds of Formula I, were correlated with those values from known substrates useful for this application.

(1) Enzyme Kinetics with cDNA-expressed CYP2D6

The evaluation of compounds of Formula I were initially performed by measuring the kinetics of turnover using cDNA-expressed CYP2D6. Vmax and Km values are important for the optimization of the assay conditions and for setting the parameters for inhibition experiments. Fluorometric assays for the turnover of compounds of Formula I by CYP2D6 were performed based on a modification of the method by Crespi et al. *Anal Biochem.* 248, 188–190, (1997), (described below). Comparisons of the enzyme kinetics (Table II) for compounds of Formula I and the substrate, 3-cyano-7-ethoxycoumarin (CEC), show that CYP2D6 has a higher affinity for compounds of Formula I (lower Km) and a higher catalytic turnover for compounds of Formula I (higher Vmax). Within the series Ia–Ic, compound Ia has the highest catalytic turnover and is therefore the most useful substrate. However, compounds Ib and Ic, contain the 4-trifluoromethyl group (R4) which shifts the fluorescent properties of these molecules to longer wavelengths. In the event that a putative inhibitor has competing fluorescent properties with compound Ia, compounds Ib and Ic are useful CYP2D substrates despite their lower catalytic turnover compared to compound Ia.

TABLE II

| Compound # | $K_m$ (uM) | $V_{max}$ (min$^{-1}$) |
| --- | --- | --- |
| CEC | 67 | 0.017 |
| Ia | 1.1 | 1.0 |
| Ib | 0.8 | 0.16 |
| Ic | 3.3 | 0.2 |

Example Compound Ia. Assays were conducted in 96 well microtiter plates (Corning COSTAR, cat. no. 3915). The substrate, compound Ia, was prepared in pH 7.4 potassium phosphate buffer (0.1 M). After substrate addition, the plates were prewarmed to 37° C. Incubations were initiated by the addition of prewarmed enzyme and cofactors. The enzymes were commercially available, baculovirus/insect cell expressed human CYP2D6 (SUPERSOMES®, GENTEST Corporation). The amount of enzyme added per well was 1.5 pmoles. The final cofactor concentrations were 0.0082 mM NADP, 0.41 mM glucose-6-phosphate and 0.2 U/ml glucose-6-phosphate dehydrogenase. Final incubation volume was 0.2 ml. Incubations were carried out for 45 minutes and stopped by the addition of 0.075 ml of 80% acetonitrile, 20% 0.5 M Tris base. Fluorescence per well was measured using a BMG FLUOstar Model 403 controlled with an IBM-compatible computer. The metabolite was measured using an excitation wavelength of 390 nm and emission wavelength of 460 nm. Data was exported and analyzed using an Excel spreadsheet. The activity was quantified by comparing to a standard curve of 3-[2-(N,N-diethylamino)ethyl]-7-hydroxy-4-methylcoumarin hydrochloride. Apparent Km and Vmax values were calculated by non-linear kinetics using SigmaPlot 4.0 software.

Example Compounds Ib and Ic. The following procedure applies to compounds Ib and Ic as substrates. Assays were conducted in 96 well microtiter plates (Corning COSTAR, cat. no. 3915). The substrates, Ib and Ic, were prepared in acetonitrile. After cofactors addition, the plates were prewarmed to 37° C. Incubations were initiated by the addition of prewarmed enzyme and substrate. The enzymes were commercially available, baculovirus/insect cell expressed human CYP2D6 (SUPERSOMES®, GENTEST Corporation). The amount of enzyme added per well was 5–10 pmoles. The final cofactor concentrations were 1.3 mM NADP, 3.3 mM glucose-6-phosphate, 3.3 mM MgCl$_2$ and 0.4 U/ml glucose-6-phosphate dehydrogenase. Final incubation volume was 0.2 ml. Incubations were carried out for 45 minutes and stopped by the addition of 0.075 ml of 80% acetonitrile, 20% 0.5 M Tris base. Fluorescence per well was measured using a BMG FLUOstar Model 403 plate scanner controlled with an IBM-compatible computer. The metabolite was measured using an excitation wavelength of 410 nm and emission wavelength of 538 nm. Data was exported and analyzed using an Excel spreadsheet. The enzyme activity was quantified by comparing to a standard curve of 3-[2-(N, N-diethyl-N-methylammonium)ethyl]-7-hydroxy-4-trifluoromethylcoumarin iodide (compound IIb) when assaying for metabolism of Ib or 3-[2-(diethylamino) ethyl]-7-hydroxy-4-trifluoromethyl coumarin (compound IIc) when assaying for metabolism of Ic. Apparent Km and Vmax values were calculated by non-linear kinetics using SigmaPlot 4.0 software.

(2) Selectivity in a Panel of cDNA-Expressed P450 Enzymes

Figure 1:
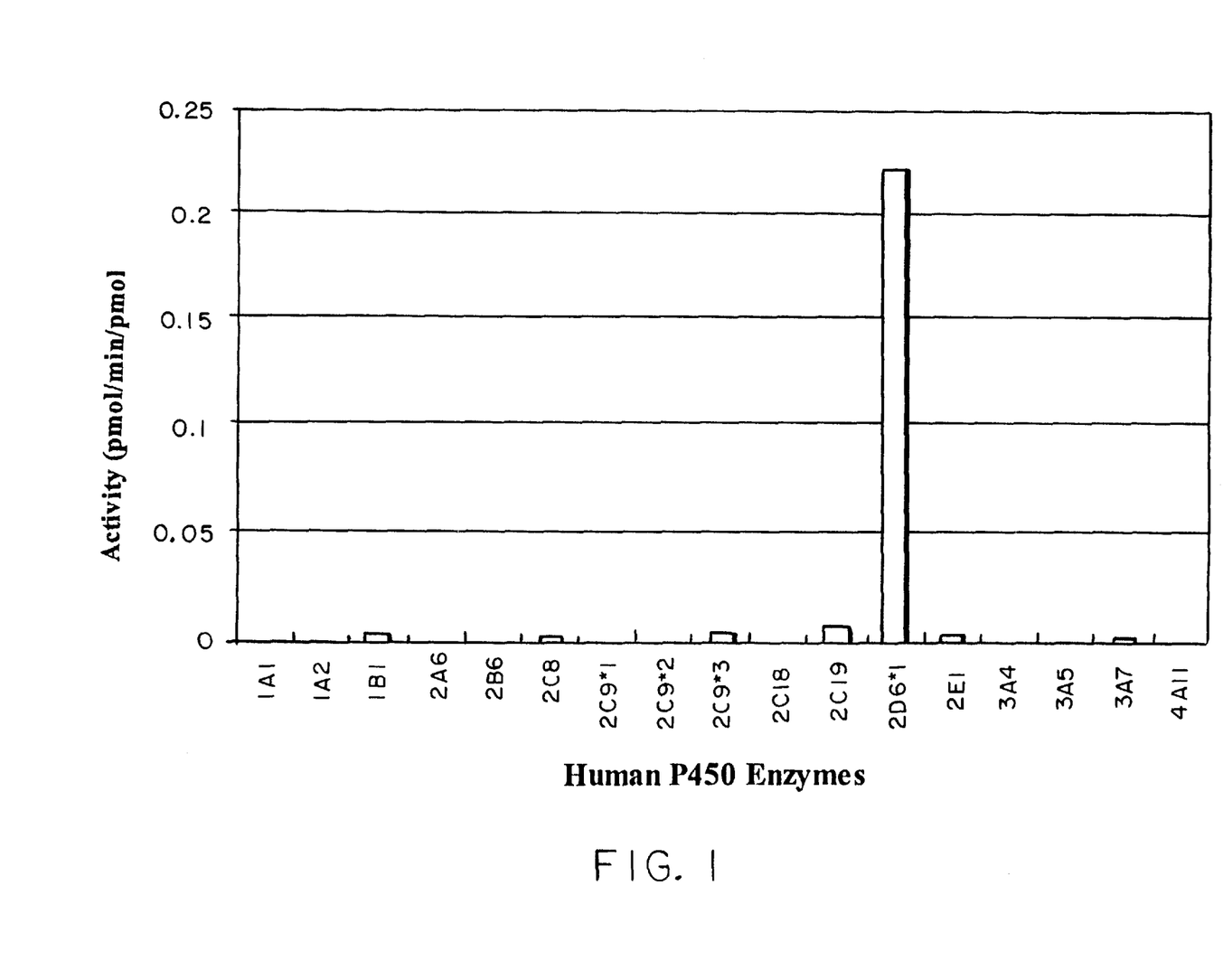
FIG. 1 is a selectivity for compound Ia dealkylation by a panel of human P450 enzymes.
Figure 2:
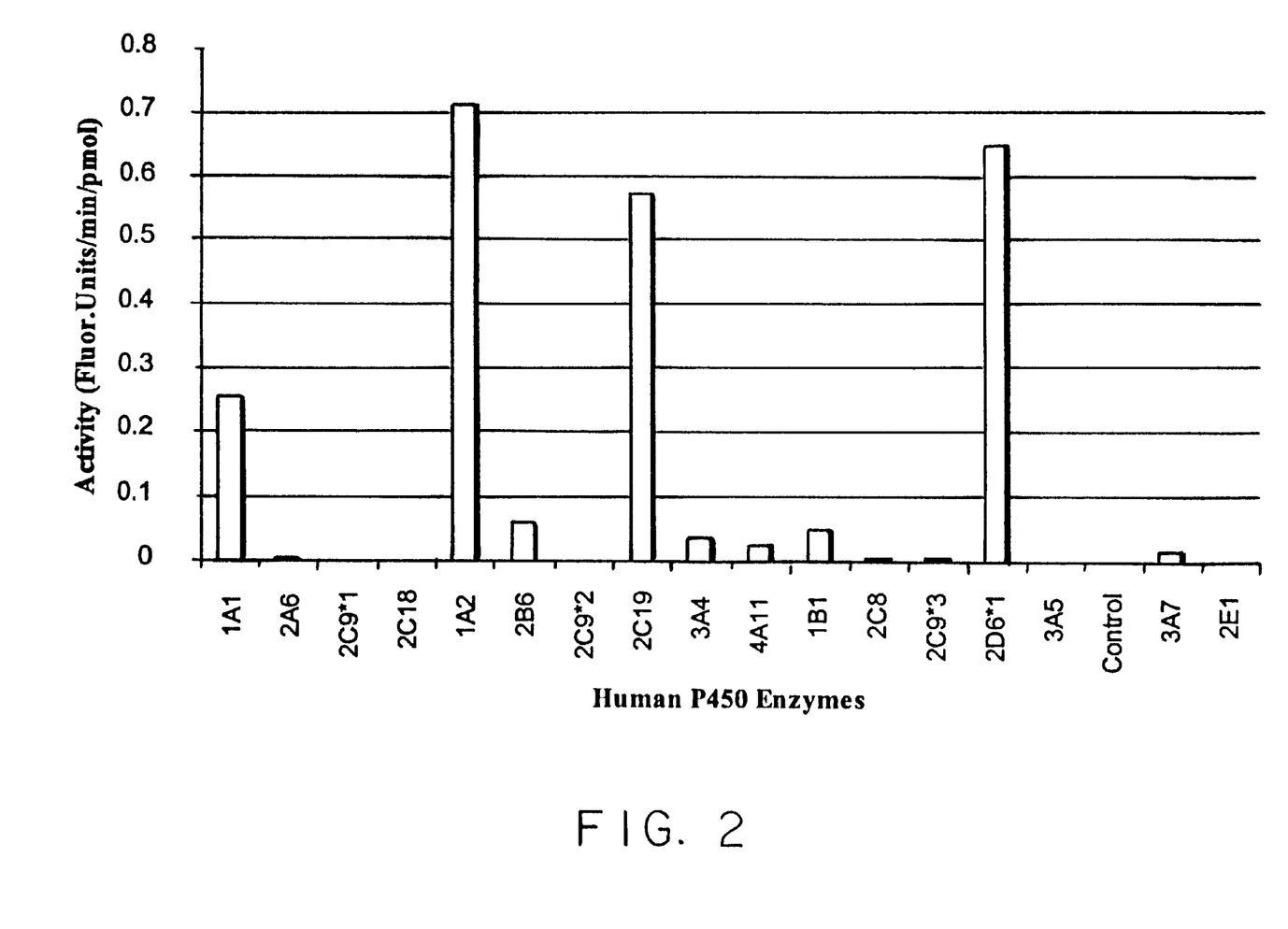
FIG. 2 is a selectivity for compound Ic dealkylation by a panel of human P450 enzymes.
Figure 3:
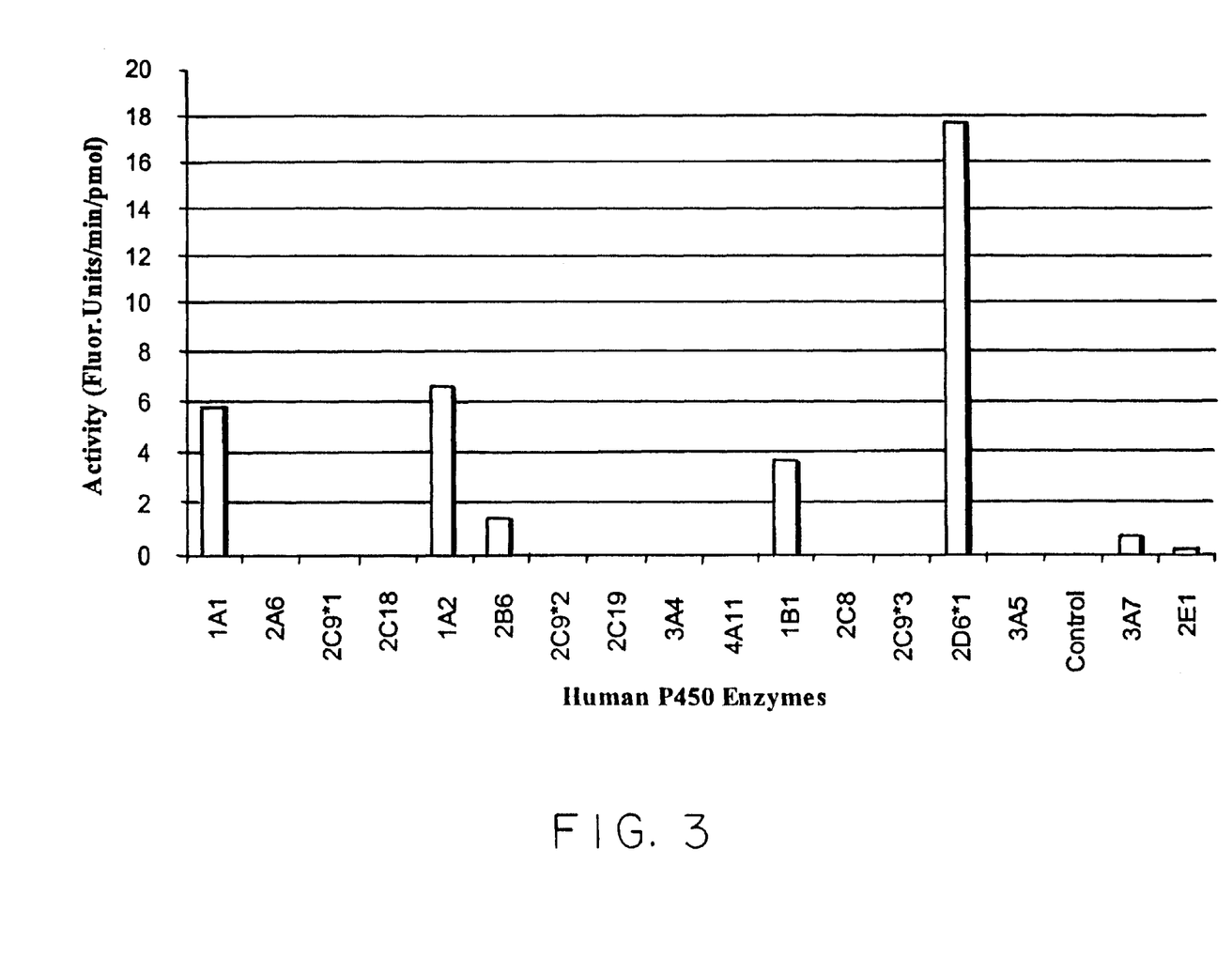
FIG. 3 is a selectivity for compound Ib dealkylation by a panel of human P450 enzymes.

The selectivity of various P450 isoforms for dealkylation of compounds Ia, Ib and Ic was examined using a panel of commercially available human cDNA-expressed enzymes. A substrate that is selective for a single P450 isoform (substrate is catalytically turned over by a single P450 isoform) is a desirable trait in that its activity may be examined within a heterogeneous mixture of enzymes, for example, in human liver microsomes. The previously published high throughput screening substrate, 3-cyano-7-ethoxycoumarin (CEC) is significantly metabolized by other human cytochromes P450 (Crespi et al. *Anal Biochem.* 248, 188–190, (1997). Comparison of the catalytic selectivity for compounds of Formula I is shown in FIGS. 1, 2, and 3. Compound Ia is selective for CYP2D6, while compounds Ib and Ic are also substrates for other human P450 enzymes. Compound Ia is therefore a more useful substrate for probing CYP2D activity in a heterogeneous mixture than compounds Ib, Ic, and the previous substrate CEC.

Example Compounds Ia, Ib and Ic. Compounds Ia, Ib and Ic were incubated as described in the examples (1) above except that the enzyme source consisted of one each of several different commercially available, baculovirus/insect cell expressed human cytochrome P450 enzymes (SUPERSOME®, GENTEST Corporation).

(3) Human Liver Microsomes

Human liver microsomes (HLM) contain several drug (xenobiotic) metabolizing cytochromes P450. When HLM are used as an enzyme source, it is critical that the probe biotransformation be specifically catalyzed by the enzyme of interest. If multiple enzymes significantly contribute to the probe biotransformation, then data interpretation is impossible. The CYP2D6 specificity of substrates of compound I were examined using HLM and the well characterized, highly potent and specific CYP2D6 inhibitor, quinidine. The measurable metabolism of compound I was found to be exclusively due to CYP2D6. Therefore, in contrast to the previously published high throughput screening substrate, 3-cyano-7-ethoxycoumarin (CEC) which is also significantly metabolized by other human cytochromes P450 (Crespi et al. *Anal Biochem.* 248, 188–190, (1997)), compound I is a specific substrate for CYP2D6.

Example Compound I. A 1.0 ml reaction containing 1.0 mg/ml CYP2D6-containing human liver microsomes (Donor H023, GENTEST Corporation), 0.0082 mM NADP+, 3.3 mM glucose-6-phosphate, 0.4 U/ml glucose-6-phosphate dehydrogenase, 3.3 mM magnesium chloride and 5.0 uM compound I in 100 mM potassium phosphate (pH 7.4), in the presence and absence of 5 uM quinidine, was incubated at 37° C. for 5, 10 and 15 minutes. After incubation, 100 ul of the reaction was added to 1.9 ml of 100 mM Tris (pH 9) and the fluorescence was determined with excitation at 390 nm and emission at 460 nm in a spectrofluorometer. The activity was quantitated by comparing to a standard curve of 3-[2-(diethylamino)ethyl]-7-hydroxy-4-methylcoumarin hydrochloride (Table III):

| Time (min) | pmole Product | pmole Product with quinidine |
|---|---|---|
| 0 | 0 | 0 |
| 5 | 3.3 | 0 |
| 10 | 6.3 | 0 |
| 15 | 8.5 | −0.7 |

(4) High Throughput CYP2D6 Inhibition Screen

The potential for measuring the CYP2D6 inhibition potential of compounds of Formula I was based on a modification of the published method by Crespi et al. *Anal Biochem.* 248, 188–190, (1997). This published study examined the $IC_{50}$ for the potent CYP2D6 inhibitor quinidine using CEC as a substrate. Good agreement was seen with published inhibition kinetics for quinidine and human liver microsomes (Zanger et.al., Biochemistry, 27, 5447–5454, (1988)). A series of CYP2D6 selective inhibitors was examined in this system, using CEC or compounds of Formula I as a substrate. $IC_{50}$ values were found to be highly correlated between CEC and compounds Ia and Ib illustrating the usefulness of these compounds as substrates for CYP2D6 inhibition.

Example Compound I. Assays were conducted in 96 well microtiter plates. The substrates, compounds of Formula I, were prepared in pH 7.4 potassium phosphate buffer or acetonitrile. The substrate stock concentrations were twice the final concentration (final concentration chosen to be approximately the apparent $K_m$, for example 2 μM for compound I). The 12 wells in a row were used for one test. Wells 1 to 8 contained serial 1:3 dilutions of the inhibitors. Wells 9 and 10 contained no inhibitor and rows 11 and 12 were blanks for background fluorescence (stop solution added before the enzyme). After substrate and inhibitor addition, the plates were prewarmed to 37° C. Incubations were initiated by the addition of prewarmed enzyme and cofactors. The enzymes were commercially available, baculovirus/insect cell expressed human CYP2D6 (SUPERSOMES®, Cat. no. P217, (GENTEST Corporation). The amount of enzyme added per well was 1.5 to 10 pmoles. The final cofactor concentrations were 8.2 μM NADP, 3.3 mM glucose-6-phosphate and 0.4 U/ml glucose-6-phosphate dehydrogenase for compound Ia or 1.3 mM NADP, 3.3 mM glucose-6-phosphate, 3.3 mM $MgCl_2$ and 0.4 U/ml glucose-6-phosphate dehydrogenase for compounds Ib and Ic. Final incubation volume was 0.2 ml. Incubations were carried out for 45 minutes and stopped by the addition of 0.075 ml of 80% acetonitrile, 20% 0.1 M Tris pH 9. Fluorescence per well was measured using a BMG FLUOstar Model 403 plate scanner controlled with an IBM-compatible computer. The metabolite was measured using an excitation wavelength of 390 nm and emission wavelength of 460 nm (compound Ia) or an excitation wavelength of 410 nm and emission wavelength of 538 nm (compounds Ib and Ic). Data was exported and analyzed using an Excel spreadsheet. The $IC_{50}$ values were calculated by linear interpolation (Tables IV and V):

TABLE IV

Test Inhibitor Compounds

| Test Inhibitor Compound | Concentration (in $dH_2O$) | Final Conc. in well #1 |
|---|---|---|
| Bufuralol | 6 mM | 300 uM |
| Debrisoquine | 6 mM | 300 uM |
| Dextromethorphan | 2 mM | 100 uM |
| Fluoxetine | 2 mM | 100 uM |
| Imipramine | 2 mM | 100 uM |
| Norfluoxetine | 2 mM | 100 uM |
| Perhexiline | 0.2 mM | 10 uM |
| Propranolol | 16 mM | 800 uM |
| Quinidine | 10 uM | 0.5 uM |
| Sparteine | 40 mM | 2 uM |

TABLE V

CYP2D6 HTS Substrates: $IC_{50}$ Values (uM)

| | Substrate | | | |
|---|---|---|---|---|
| Inhibitor | CEC | Ia | Ib | Ic |
| Bufuralol | 27 | 17 | 23.3 | 104 |
| Debrisoquine | 29 | 20 | 10.6 | 105 |
| Dextromethorphan | 2.3 | 3.1 | 6.6 | 34 |
| Fluoxetine | 3.2 | 0.79 | 1.3 | 22 |
| Imipramine | 2.2 | 3.6 | 4.5 | 50 |
| Norfluoxetine | 8.4 | 1.1 | not done | not done |
| Perhexiline | 0.87 | 0.34 | 1.6 | 4.8 |
| Propranolol | 2.2 | 2.9 | 8.7 | 56 |
| Quinidine | 0.006 | 0.014 | 0.038 | 0.21 |
| Sparteine | 12.1 | 37.7 | 44 | 676 |

The preceding is merely a detailed description of certain preferred embodiments. It therefore should be apparent to those skilled in the art that various modifications and equivalents can be made without departing from the spirit or scope of the invention.

What is claimed is:

1. A compound of the Formula I:

(a) wherein $R^1$ is selected from the group consisting of a hydrogen and a halide;
(b) wherein $R^2$ is selected from the group consisting of an alkyl and an aryl;
(c) wherein $R^3$ is selected from the group consisting of a hydrogen and a halide;
(d) wherein $R^4$ is selected from the group consisting of a hydrogen, an alkyl, and an aryl;
(e) wherein $R^5$ is selected from the group consisting of a hydrogen and an alkyl;
(f) wherein $R^6$ is an alkyl;
(g) wherein $R^7$ is an alkyl;
(h) wherein n is a whole number selected from the group consisting of 0, 1, 2, 3, and 4;

(i) wherein m is 1; and (j) wherein $X^{-1}$ is a negatively charged counter ion.

2. The compound of claim 1, wherein $R^1$ is a halide.

3. The compound of claim 1, wherein $R^1$ is a hydrogen.

4. The compound of claim 1, wherein $R^2$ is an alkyl.

5. The compound of claim 1, wherein $R^3$ is a halide.

6. The compound of claim 1, wherein $R^3$ is a hydrogen.

7. The compound of claim 1, wherein $R^4$ is selected from the group consisting of a hydrogen and an alkyl.

8. The compound of claim 1, wherein $R^4$ is a hydrogen.

9. The compound of claim 1, wherein $R^5$ is selected from the group consisting of a hydrogen and an alkyl.

10. The compound of claim 1, wherein $R^5$ is a hydrogen.

11. The compound of claim 1, wherein $R^6$ is selected from the group consisting of methyl, ethyl and propyl.

12. The compound of claim 1, wherein $R^7$ is selected from the group consisting of methyl, ethyl and propyl.

13. The compound of claim 1, wherein n is 2.

14. The compound of claim 1, wherein the compound has a Km of greater than about 50 nM with a Vmax greater than about 0.05 $min^{-1}$ for a CYP2D-catalyzed reaction.

15. The compound of claim 1, wherein the compound is selected from the group consisting of compounds in which:

$R^1$ and $R^3$ are fluoro;

$R^2$ is methyl, ethyl, or benzyl; and $R^4$ is trifluoromethyl or cyano.

16. A composition comprising a compound of claim 1, wherein the compound is present in the composition at a concentration greater than at least 50% by weight.

17. A compound having the formula 3-[2-(N,N-diethyl-N-methylammonium)ethyl]-7-methoxy-4-methylcoumarin (AMMC, $C_{18}H_{26}NO_3$).

* * * * *